(12) United States Patent
Kobayashi et al.

(10) Patent No.: US 11,064,868 B2
(45) Date of Patent: Jul. 20, 2021

(54) ENDOSCOPE WITH DISTAL LINEAR CONDUCTOR

(71) Applicant: PANASONIC I-PRO SENSING SOLUTIONS CO., LTD., Fukuoka (JP)

(72) Inventors: Katsuhiro Kobayashi, Fukuoka (JP); Hirofumi Enomoto, Fukuoka (JP); Kouichi Hoshino, Fukuoka (JP)

(73) Assignee: PANASONIC I-PRO SENSING SOLUTIONS CO., LTD., Fukuoka (JP)

( * ) Notice: Subject to any disclaimer, the term of this patent is extended or adjusted under 35 U.S.C. 154(b) by 337 days.

(21) Appl. No.: 16/052,209

(22) Filed: Aug. 1, 2018

(65) Prior Publication Data

US 2019/0038112 A1 Feb. 7, 2019

(30) Foreign Application Priority Data

Aug. 2, 2017 (JP) .............................. JP2017-150016

(51) Int. Cl.
*A61B 1/00* (2006.01)
*A61B 1/05* (2006.01)
(Continued)

(52) U.S. Cl.
CPC ........ *A61B 1/00096* (2013.01); *A61B 1/0008* (2013.01); *A61B 1/05* (2013.01);
(Continued)

(58) Field of Classification Search
CPC ..... A61B 1/00096; A61B 1/0008; A61B 1/05; A61B 1/00165; A61B 1/07; A61B 1/233;
(Continued)

(56) References Cited

U.S. PATENT DOCUMENTS 9,848,757 B2 12/2017 Haraguchi et al.
10,278,565 B2 * 5/2019 Wieters .............. A61B 1/00114
(Continued)

FOREIGN PATENT DOCUMENTS

JP 2004-148028 A 5/2004
JP 2013-198566 A 10/2013
(Continued)

OTHER PUBLICATIONS

Search Report issued in European Patent Office (EPO) Patent Application No. 18186023.0, dated Jan. 7, 2019.
(Continued)

*Primary Examiner* — Timothy J Neal
*Assistant Examiner* — William B Chou
(74) *Attorney, Agent, or Firm* — Greenblum & Bernstein P.L.C.

(57) ABSTRACT

An endoscope includes an insertion portion that has a tip portion to be inserted into an examination target from a tip side of the tip portion. The endoscope includes a lens unit that is disposed at the tip portion. The endoscope includes an image sensor that is disposed on an opposite side to the tip side of tip portion with respect to the lens unit. The endoscope includes a linear conductor that has a tip disposed at the tip side with respect to the image sensor and has a proximal end which is extended from the tip through inside the insertion portion.

13 Claims, 12 Drawing Sheets

(51) Int. Cl.
  *G02B 23/24* (2006.01)
  *A61B 1/07* (2006.01)
  *A61B 1/267* (2006.01)
  *A61B 1/307* (2006.01)
  *A61B 1/313* (2006.01)
  *A61B 1/233* (2006.01)

(52) U.S. Cl.
  CPC ..... *G02B 23/2423* (2013.01); *G02B 23/2476* (2013.01); *G02B 23/2484* (2013.01); *A61B 1/00165* (2013.01); *A61B 1/07* (2013.01); *A61B 1/233* (2013.01); *A61B 1/267* (2013.01); *A61B 1/307* (2013.01); *A61B 1/3137* (2013.01)

(58) Field of Classification Search
  CPC ....... A61B 1/267; A61B 1/307; A61B 1/3137; G02B 23/2423; G02B 23/2476; G02B 23/2484
  See application file for complete search history.

(56) References Cited

U.S. PATENT DOCUMENTS

| | | | |
|---|---|---|---|
| 2004/0092793 A1 | 5/2004 | Akai | |
| 2007/0173695 A1* | 7/2007 | Hirata | A61B 1/0615 600/152 |
| 2007/0230075 A1* | 10/2007 | Murata | H02H 9/008 361/58 |
| 2009/0227842 A1* | 9/2009 | Ando | A61B 1/0055 600/146 |
| 2013/0303853 A1 | 11/2013 | Takahashi et al. | |
| 2016/0213239 A1* | 7/2016 | Fujii | A61B 1/0019 |
| 2016/0345806 A1* | 12/2016 | Ishii | A61B 1/00071 |
| 2016/0353976 A1* | 12/2016 | Makiyama | G02B 23/2476 |
| 2016/0367122 A1* | 12/2016 | Ichimura | A61B 1/051 |
| 2017/0150873 A1* | 6/2017 | Tatebayashi | G02B 23/24 |
| 2017/0265715 A1 | 9/2017 | Nishina et al. | |
| 2019/0133558 A1* | 5/2019 | Morimoto | A61B 8/4494 |

FOREIGN PATENT DOCUMENTS

| | | |
|---|---|---|
| JP | 2017-047168 A | 3/2017 |
| WO | WO2013/031276 A1 | 3/2013 |
| WO | 2016/203830 A1 | 12/2016 |

OTHER PUBLICATIONS

Office Action issued in Japanese Counterpart Patent Appl. No. 2017-150016, dated Mar. 9, 2021, along with an English translation thereof.

* cited by examiner

ENDOSCOPE WITH DISTAL LINEAR CONDUCTOR

BACKGROUND OF THE INVENTION

1. Field of the Invention

The present disclosure relates to an endoscope.

2. Description of the Related Art

In recent years, in the medical field or the industrial field, endoscopes for imaging an observation target (for example, the inside of a patient's body or the inside of an apparatus or a structure) have become widespread. In this type of endoscope, in an insertion portion on a tip side to be inserted into the inside of an observation target, light from an imaging region is focused on a light-receiving surface of an image sensor by an objective lens system. The endoscope converts the focused light into electrical signals, and sends the electrical signals to an external image processor or the like as video signals via a signal cable.

For example, in endoscopes to be used in the medical field, in order to alleviate a patient's burden, it is important to further reduce the external diameter of the insertion portion on the tip side to be inserted into the inside of a patient's body or the like. In the related art, oral endoscopes having a normal diameter had a maximum external diameter of about 8 to 9 mm. For this reason, there was a case where a tongue base was likely to be touched during insertion and a patient are accompanied by nausea or stuffiness. Thus, in recent years, fine-diameter transnasal endoscopes have rapidly spread. In the fine-diameter transnasal endoscopes, the maximum external diameter is about 5 to 6 mm of about half of the related-art oral endoscopes. For this reason, in the fine-diameter transnasal endoscopes, transnasal insertion is possible. As a result, in cooperation with being as thin as about 5 mm, in many cases, vomiting reflex is little and insertion is also not bothered too much.

Here, in endoscopes into which an imaging unit including an objective lens system, an image sensor, and the like are incorporated, for example, WO2013/031276 suggests an endoscope that displays an image (endoscopic image) obtained by imaging the observation target on a display device, such as an external monitor.

Main portions of an endoscope 501 disclosed in WO2013/031276 are illustrated in FIG. 14. FIG. 14 is a sectional view illustrating the configuration of a tip portion of the related-art endoscope 501.

An imaging unit 505 is built in a tip rigid portion 503 of the endoscope 501. The imaging unit 505 has an objective lens group 507, and a substantially tubular lens frame 509 that is a fixing frame holding the objective lens group 507. In the imaging unit 505, imaging light on an optical axis O incident on the objective lens group 507 is focused on a light receiving portion 513 of a solid-state image sensor 511.

In the endoscope 501, the tip rigid portion 503 of a tip portion 515 is formed of non-conductive hard resin. Additionally, the endoscope 501 is provided with a pipe 517 made of resin, such as rubber, which is provided continuously with the rear of the tip rigid portion 503, and a metallic pipe 519 disposed on an inner surface of the resin pipe 517.

The tip rigid portion 503 includes two projection portions 521 that extend upward and downward. The projection portions 521 extend to two upper and lower locations so as to approach the metallic pipe 519 in a contactless manner, and a separation distance G thereof from the metallic pipe 519 is set to about 0.2 mm.

In the endoscope 501 configured as described above, static electricity from the tip rigid portion 503 is discharged to the metallic pipe 519 via the two projection portions 521. Then, electric charges of the applied static electricity safely flow from the metallic pipe 519 or the bending tube of a bending portion to a ground (GND) of a subsequent state video processor (not illustrated) through a shield of a flexible tube portion. Accordingly, the endoscope 501 can be configured such that an electrical configuration within the tip portion, in this example, the static electricity toward the solid-state image sensor 511 is not easily discharged.

The related-art endoscope 501 as shown in WO2013/031276 can be configured such that the static electricity is not easily discharged toward the solid-state image sensor 511. However, in the endoscope 501, the solid-state image sensor 511 is covered with the substantially tubular lens frame 509, and the outsides of the two upward and downward extending projection portions 521 of the lens frame 509 are further surrounded by the metallic pipe 519. For this reason, there is a possibility that it is difficult to realize a reduction in size or a reduction in diameter of the insertion tip portion of the endoscope 501. In other words, there is a possibility to it is difficult to achieve the compatibility between protecting the image sensor by allowing the static electricity to escape and realizing a reduction in size or a reduction in diameter of the insertion tip portion of the endoscope.

SUMMARY OF THE INVENTION

The present disclosure has been invented in view of the above-described related-art situation, and an object thereof is to provide an endoscope in which a reduction in diameter of an insertion tip portion is facilitated with a simple structure while an image sensor is protected by allowing static electricity to escape.

The present disclosure provides an endoscope including an insertion portion that has at least a tip portion to be inserted into an examination target from a tip side of the tip portion; a lens unit that is disposed at the tip portion; an image sensor that is disposed on an opposite side to the tip side of the tip portion with respect to the lens unit; and a linear conductor that has a tip disposed at the tip side with respect to the image sensor and has a proximal end which is extended from the tip through inside the insertion portion.

According to the present disclosure, a reduction in diameter of the insertion tip portion can be facilitated with a simple structure while the image sensor is protected by allowing the static electricity to escape.

DETAILED DESCRIPTION OF THE PREFERRED EMBODIMENTS

Figure 1:
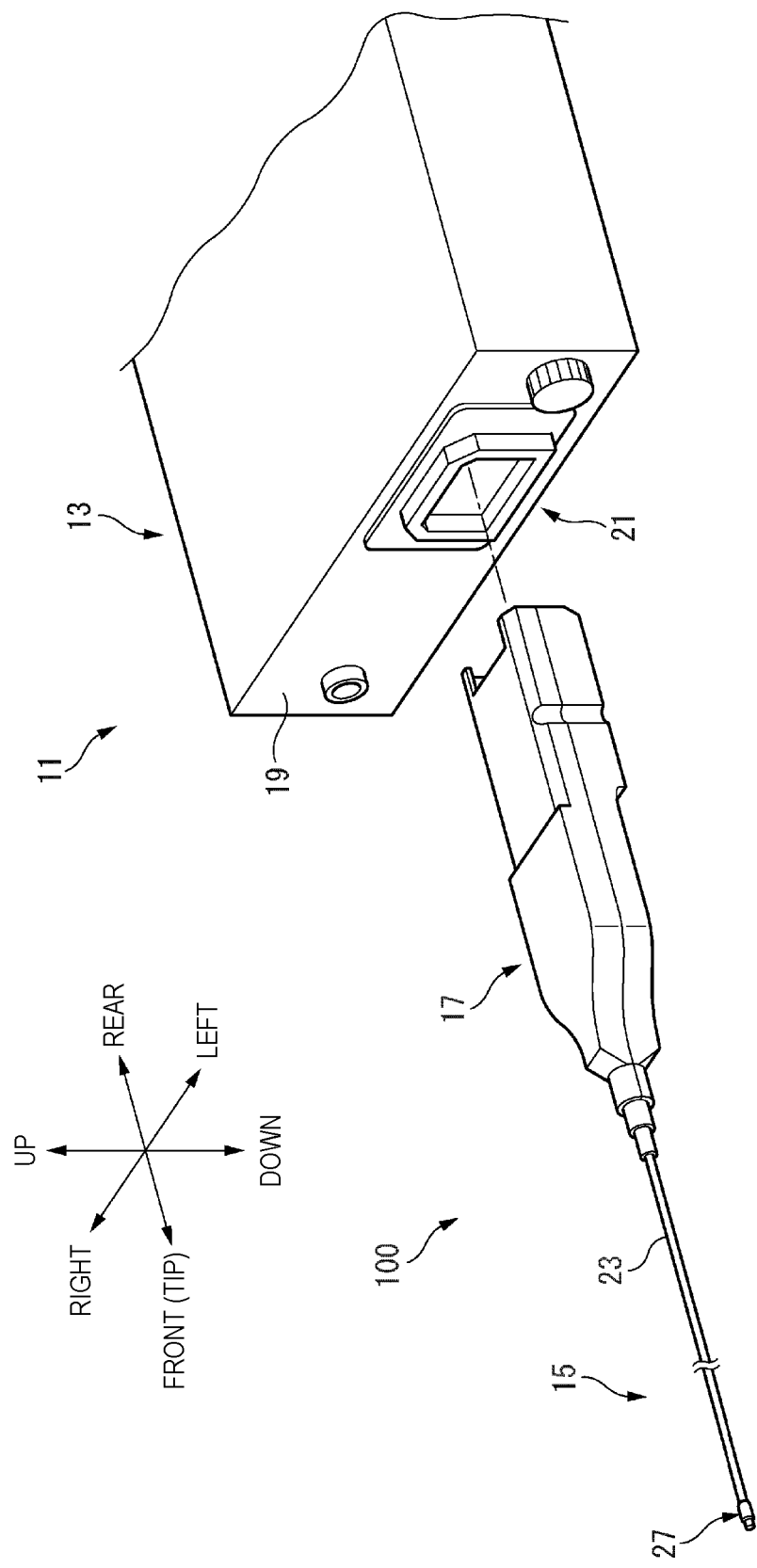
FIG. 1 is an overall configuration view illustrating an example of an endoscopic system using an endoscope of Embodiment 1.

Background Leading to Contents of Respective Embodiments

Compared to the maximum external diameter of the above-described oral endoscopes and fine-diameter transnasal endoscopes, in recent years, in order to observe the inside of an ultrafine diameter region (for example, the inside of a blood vessel of a human body) that cannot be inserted within the related-art oral endoscopes and fine-diameter transnasal endoscopes, development of a further reduction in diameter is important. For example, a high-quality endoscope in which the maximum external diameter of an insertion tip portion capable of observing the inside of the blood vessel of the human body, or the like, is 2 mm or less is required.

Additionally, as an existing endoscope, for example, there is known a fiber mirror type endoscope in which an insertion tip portion is not provided with an image sensor (that is, an image sensor), an optical image is guided from the insertion tip portion to a rear end side by a bundle of optical fibers, and the optical image is focused on an image sensor provided on a rear end side that is not the insertion tip portion. In this type of endoscope, there is an endoscope of which the maximum external diameter of the insertion tip portion is 2 mm or less. However, in such a type of endoscope, restrictions of the thickness and number of optical fibers, boundary line patterns of optical fibers adjacent to each other in a captured image are conspicuous. Therefore, it is difficult to realize the high resolution and high quality of the captured image.

Meanwhile, in a related-art endoscope like the above-described WO2013/031276, a gap has provided in a diameter direction of the insertion tip portion. For this reason, there are manufacturing problems that the maximum external diameter increases, crushing is likely to occur due to an external force or bending, it is difficult to guarantee insulation against static electricity, parts shapes are complicated, and assembling is difficult. Additionally, in this related-art endoscope, since the metallic pipe is provided, similarly, there is a possibility that the maximum external diameter increases and the flexibility of an insertion portion is impaired.

Thus, in the respective following embodiments, examples of endoscopes in which a reduction in diameter of the insertion tip portion is facilitated with a simple structure while the image sensor is protected by releasing static electricity will be described.

Hereinafter, the respective embodiments specifically disclosing the endoscopes of the present disclosure will be described in detail, referring to the drawings appropriately. However, there is a case where detailed description more than needed is omitted. For example, there is a case where detailed description of already well-known matters and duplicate description of substantially the same configuration are omitted. This is to avoid unnecessary redundancy of the following description and facilitate understanding by those skilled in the art. In addition, the accompanying drawings and the following description are provided so that those skilled in the art sufficiently understand the present disclosure, and are not intended to limit the subject matter described in the claims by these drawings and description.

Embodiment 1

FIG. 1 is an overall configuration view illustrating an example of an endoscopic system 11 using an endoscope 100 of Embodiment 1. In FIG. 1, the overall configuration of the endoscopic system 11 including the endoscope 100 and a video processor 13 are illustrated in a perspective view.

In addition, directions to be used for description in the present specification follow description of directions in the respective drawings. Here, the "up" and the "down" correspond to above and below the video processor 13 placed on a horizontal plane, respectively, and the "front (tip)" and the "rear" correspond to a tip side of an insertion portion 15 of an endoscope body (hereinafter referred to as an "endoscope" and a proximal end side (in other words, a video processor 13 side) of a plug 17, respectively.

As illustrated in FIG. 1, the endoscopic system 11 is configured to include, for example, the endoscope 100 that is a medical flexible endoscope, and the video processor 13 that performs well-known image processing or the like on a still image or a moving image captured by imaging the inside of an observation target (for example, the blood vessel of the human body) serving as an example of an examination target. The endoscope 100 extends substantially in a forward-rearward direction, and includes the insertion portion 15 to be inserted into the inside of the observation target, and the plug 17 to which a rear portion of the insertion portion 15 is connected.

The video processor 13 has a socket 21 that opens in a front wall 19. A rear portion of the plug 17 of the endoscope 100 is inserted into the socket 21. Accordingly, the endoscope 100 is capable of transmitting and receiving electrical power and various signals (video signals, control signals, and the like) between the endoscope 100 and the video processor 13.

The above-described electrical power and various signals are transmitted from the plug 17 to a flexible portion 23 via a transmission cable 25 (refer to FIG. 3 or 4) inserted through the inside of the flexible portion 23. Image data captured by the image sensor 29 (that is, the image sensor) provided in a tip portion 27 is transmitted from the plug 17 to the video processor 13 via the transmission cable 25. The video processor 13 performs well-known image processing, such as color correction and grayscale correction, on the image data transmitted from the plug 17, and outputs the image data after the image processing to a display device (not illustrated). The display device is, for example, a monitoring device having a display device, such as a liquid crystal display panel, and displays an image (for example, data of a still image or a moving image showing a state within a blood vessel of a person who is a subject) of a subject imaged by the endoscope 100.

The insertion portion 15 has the flexible portion 23 of which a rear end is connected to the plug 17, and the tip portion 27 connected to a tip of the flexible portion 23. The flexible portion 23 has a suitable length corresponding to methods, such as various kinds of endoscopy or endoscopic surgery, and an outer periphery of the flexible portion 23 is covered with, for example, a sheath. The flexible portion 23 connects the tip portion 27 and the plug 17 to each other.

The endoscope 100 of Embodiment 1 to be described below is capable of being inserted into a fine-diameter body cavity by providing the external diameter of the tip portion 27 with a fine diameter. The fine-diameter body cavity is not limited to a blood vessel of a human body, and includes, for example, a ureter, a pancreatic duct, a bile duct, bronchioles, and the like. That is, the endoscope 100 is capable of being inserted into the blood vessel, a ureter, a pancreatic duct, a bile duct, a bronchus, and the like of a human body. In other words, the endoscope 100 can be used for observation of a lesion within the examination target (for example, a blood vessel), for example, as medical applications. The endoscope 100 is also effective in identifying atherosclerotic plaque. Additionally, the endoscope 100 is also applicable to endoscopic observation at the time of cardiac catheterization examination. Moreover, the endoscope 100 is also effective in detection of thrombus or arteriosclerotic yellow plaque. In addition, an arteriosclerotic lesion, a color tone (white, pale yellow, or yellow) and a surface (smoothness or irregularity) are observed. In the thrombus, a color tone (red, white, dark red, yellow, brown, or mixed color) is observed.

Additionally, the endoscope 100 can be used for diagnosis and treatment of the renal pelvis and ureter cancer, and idiopathic renal bleeding. In this case, the endoscope 100 can be inserted into the bladder from the urethra and can be further advanced even into the ureter to observe the inside of the ureter and the renal pelvis.

Additionally, the endoscope 100 is capable of being inserted into the Vater's papilla opening to the duodenum. Bile is made from the liver and passes through the bile duct, and the pancreatic juice is made from the pancreas and is discharged from the Vater's papilla in the duodenum through the pancreatic duct. The endoscope 100 is capable of being inserted from the Vater's papilla, which is an opening portion of the bile duct and the pancreatic duct, to observe the bile duct or the pancreatic duct.

Moreover, the endoscope 100 is capable of being inserted into the bronchus. The endoscope 100 is inserted from the oral cavity or the nasal cavity of a supine specimen (that is, a patient). The endoscope 100 passes over the pharynx and the larynx and is inserted into the trachea while viewing the vocal cords. The bronchus becomes narrower whenever the bronchus branches. For example, according to the endoscope 100 having a maximum external diameter of 2 mm or less, it is possible to check an inner cavity up to a sub-region bronchus.

Figure 2:
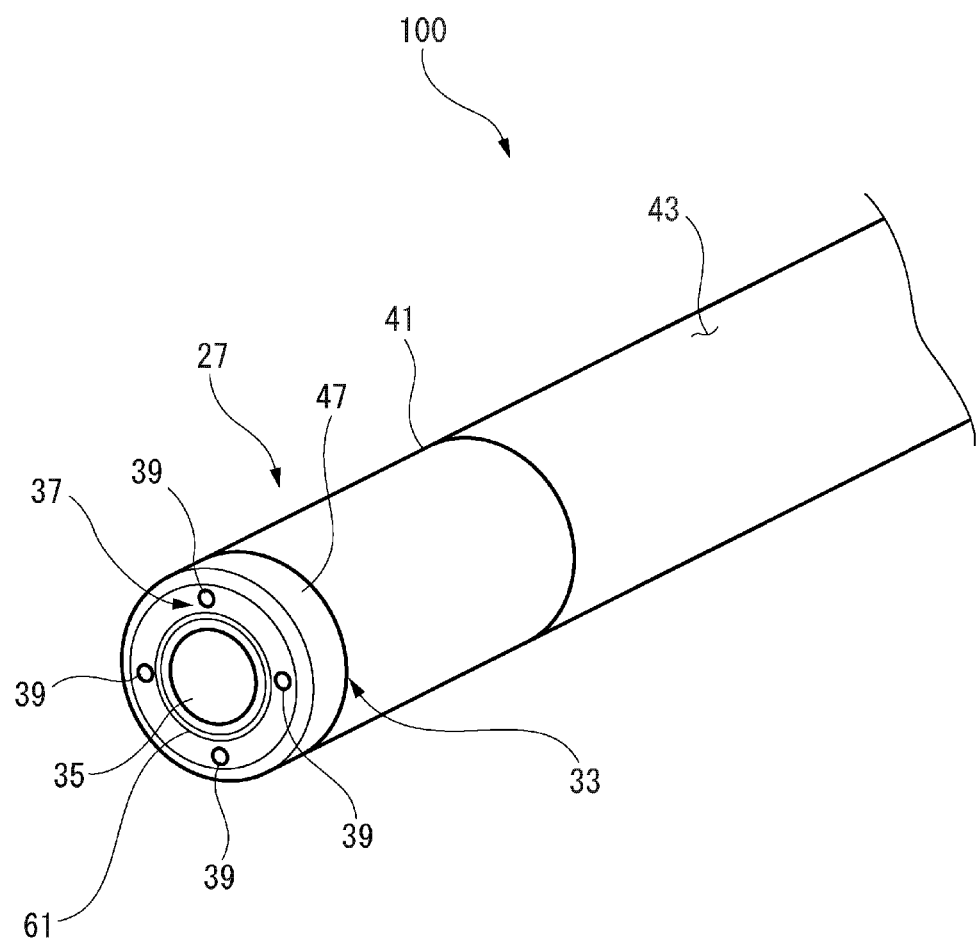
FIG. 2 is a perspective view illustrating a state in which a tip portion of the endoscope of Embodiment 1 is seen from a front side.

FIG. 2 is a perspective view illustrating a state in which the tip portion 27 of the endoscope 100 of Embodiment 1 is seen from a front side.

The endoscope 100 has a tip flange portion 33 on a front surface of the tip portion 27. In the tip flange portion 33, a lens 35 is exposed, and a plurality (for example, four) optical fibers 39 constituting a light guide 37 are disposed in a state where the optical fibers are disposed at equal intervals. The rear of the tip flange portion 33 is covered with a cover tube 41. The rear of the cover tube 41 is connected to a sheath 43. The cover tube 41 and the sheath 43 may be integrally molded.

Figure 3:
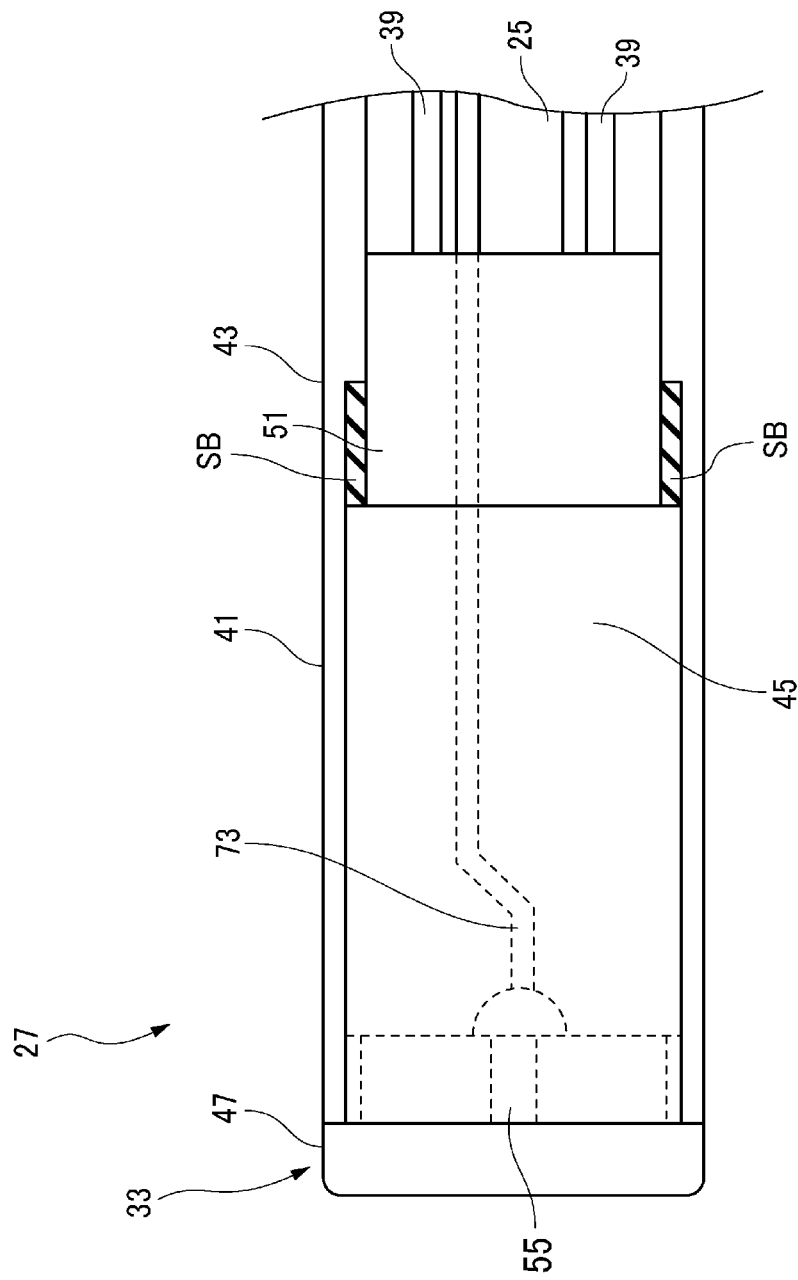
FIG. 3 is a side view of the tip portion from which half faces of a cover tube and a sheath in the endoscope of Embodiment 1 are removed.

FIG. 3 is a side view of the tip portion 27 from which half faces of the cover tube 41 and the sheath 43 in the endoscope 100 of Embodiment 1 are removed.

The cover tube 41 of the tip portion 27 covers a mold portion 45. The cover tube 41 is formed with the same external diameter as or substantially the same external diameter as the tip flange portion 33. The cover tube 41 is formed of, for example, metal, resin, or the like as a material. The cover tube 41 has a total length such that a tip thereof abuts against a larger-diameter portion 47 of the tip flange portion 33 and a rear end thereof reaches a tip of a resin portion or the transmission cable 25 that encapsulates a conductor connecting portion that joins the image sensor 29 and the transmission cable 25 together. That is, the mold portion 45 is covered with the cover tube 41.

In addition, if the distance between the rear end of the cover tube 41 and the image sensor 29 is short in a case where the cover tube 41 is formed using metal, there is a possibility that static electricity is applied from the rear end of the cover tube 41 to the image sensor 29. For this reason, it is preferable that the cover tube 41 has a length such that the rear end thereof is disposed at a position sufficiently separated from the image sensor 29. Accordingly, since it is ensured that the distance from the rear end of the cover tube 41 to the image sensor 29 is sufficiently separated, the application of the static electricity from the rear end of the cover tube 41 to the image sensor 29 is suppressed.

The mold portion 45 covered with the cover tube 41 has a smaller-diameter extending portion 51 that extends rearward of the mold portion 45. The smaller-diameter extending portion 51 is molded in a columnar shape and has, for example, four optical fibers 39 embedded therein. The smaller-diameter extending portion 51 has the four optical fibers 39 embedded inside the transmission cable 25. Internal diameter sides of the cover tube 41 and the sheath 43 are fixed to outer peripheries of the mold portion 45 and the smaller-diameter extending portion 51 with an adhesive (for example, refer to adhesive SB) or the like. That is, in the endoscope 100, the tip flange portion 33, the cover tube 41, and the sheath 43 are coaxially connected together.

In the endoscope 100, at least a portion of a lens unit 53, the image sensor 29, a portion of the transmission cable 25, and portions of the optical fibers 39 are covered with and fixed by the resin of the mold portion 45. The mold portion 45 is made of, for example, a resin material containing an additive for suppressing the transmittance of light or the like in order to avoid extra incident light to a resin material or the like or the image sensor 29. Accordingly, the thickness of the mold portion 45 can be made small and the size of the endoscope 100 can be reduced. As the additive, for example, carbon black can be added to a mold resin material (epoxy-based resin).

The sheath 43 is made of a resin material having flexibility. The sheath 43 can be provided with a single line, a plurality of wires, and braided tensile strength wire on an inner peripheral side thereof for the purpose of imparting strength. As the tensile strength wire, aramid fiber, such as poly-p-phenylene terephthalamide fiber, polyarylate fiber, polyparaphenylene benzobisoxazole fiber, polyester fiber, such as a polyethylene terephthalate fiber, nylon fiber, thin tungsten line, or thin stainless steel line can be used as an example.

Figure 4:
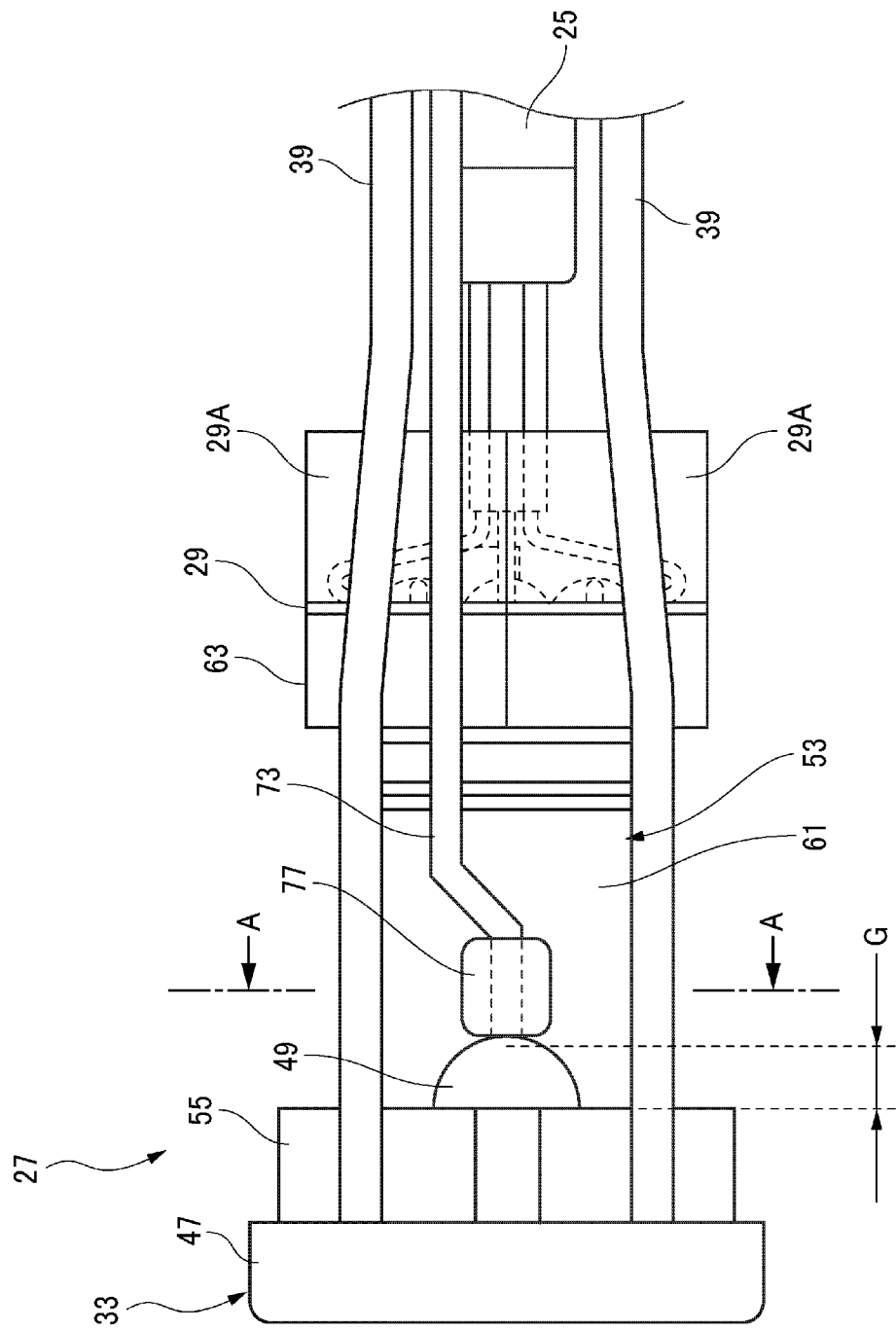
FIG. 4 is a side view of the tip portion from which a mold portion of Embodiment 1 is omitted.

FIG. 4 is a side view of the tip portion 27 from which the mold portion 45 of Embodiment 1 is omitted.

Figure 5:
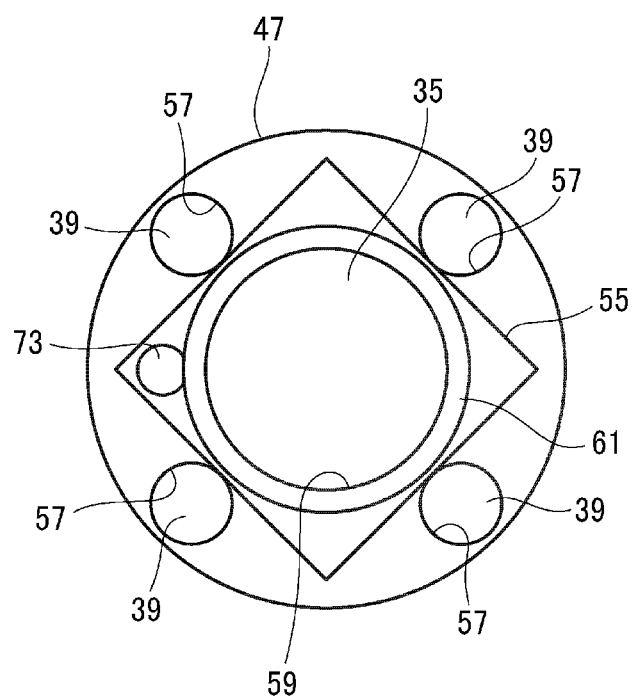
FIG. 5 is a view as seen from arrow A-A of FIG. 4.

The tip flange portion 33 is formed of, for example, stainless steel, and has conductivity. The tip flange portion 33 is formed in a tubular shape in which the larger-diameter portion 47 and an angular tube portion 55 are connected together from the tip side. The larger-diameter portion 47 has fiber holding holes 57 (refer to FIG. 5) into which the four optical fibers 39 are inserted, respectively. In addition, the larger-diameter portion 47 of the tip flange portion 33 is not limited to being formed in an annular shape as illustrated in FIG. 5, and may be formed, for example, in each of an elliptical shape, a quadrangular shape, and an octagonal shape. Particularly in a case where the larger-diameter portion 47 is formed in a quadrangular shape or an octagonal shape, it is preferable that the larger-diameter portion 47 are chamfered so as to have rounded portions without forming corner portions of the quadrangular shape or the octagonal shape as much as possible. Additionally, the larger-diameter portion 47 of the tip flange portion 33 may be cut and formed in a D-shape in at least one point, for example in a portion of an annular structure. Even in this case, it is preferable that the point cut in the D-shape is chamfered so as to have a rounded portion without forming a corner portion as much as possible. The fiber holding holes 57 expose light emitting end surfaces of the inserted optical fibers 39 to the front surface of the tip portion 27. Four fiber holding holes 57 are provided, for example, at equal intervals in the circumferential direction. The optical fibers 39 of which tip sides are inserted into the fiber holding holes 57 are delivered rearward along the lens unit 53. The angular tube portion 55 is provided with an internal diameter hole 59 (refer to FIG. 5) into which the lens unit 53 is inserted, and the lens unit 53 is inserted into the internal diameter hole 59. An object side of the lens unit 53 is supported by the internal diameter hole 59 of the tip flange portion 33. The tip flange portion 33 coaxially holds the lens unit 53.

The endoscope 100 includes the lens unit 53 that accommodates the lens 35 in a lens supporting member 61, and the image sensor 29 that has an imaging surface covered with an element cover glass 63 and is disposed on a side opposite to the object side (examination target side) of the lens unit 53. Additionally, the endoscope 100 further includes a bonding resin that fixes the lens unit 53, in which an optical axis of the lens 35 is made to coincide with the center of the imaging surface, and the element cover glass 63. Additionally, the endoscope 100 further includes the transmission cable 25 having four electric wires that are respectively connected to, for example, four conductor connecting portions provided on a surface (rear end surface) on a side (that is, a rear side) opposite to the imaging surface of the image sensor 29. The four conductor connecting portions connect respective corresponding electric wires to the rear end surface of the image sensor 29, and are fixed to the rear end surface of the image sensor 29 with a reinforcing adhesive 29A.

A single or a plurality of lenses 35 that are formed of an optical medium (for example, glass, resin, or the like), and a diaphragm (not illustrated) overlapped with the lenses 35 are incorporated into the lens supporting member 61 along the optical axes. The diaphragm is provided for adjustment of the amount of incident light to the lenses 35, and only the light that has passed through the diaphragm is capable of entering the image sensor 29.

As a metallic material that constitutes the lens supporting member 61, for example, nickel is used. Nickel has a high modulus of rigidity and relatively high corrosion resistance, and is suitable as a material that constitutes the tip portion 27. Additionally, it is preferable that the periphery of the lens supporting member 61 is uniformly covered with resin and the tip portion 27 is subjected to biocompatible coating before examination or before surgery such that the nickel constituting the lens supporting member 61 is not directly exposed from the tip portion 27 at the time of examination or surgery using the endoscope 100. Instead of nickel, for example, a copper nickel alloy may be used. The copper nickel alloy also has a high corrosion resistance and is suitable as a material that constitutes the tip portion 27. Additionally, as the metallic material that constitutes the lens supporting member 61, a material that can be manufactured by electroforming (electroplating) is preferably selected. Here, the reason why the electroforming is because the accuracy of dimensions of a member to be manufactured by the electroforming is as extremely high as less than (so-called submicron accuracy) 1 μm and variations when a number of members are manufactured are also small. Additionally, as the metallic material that constitutes the lens supporting member 61, stainless steel (for example, SUS316) may be used. It is considered that stainless steel (called an SUS tube) has high biocompatibility, and is suitable as, for example, an endoscope to be inserted into a fine-diameter region, such as a human body's blood vessel. The lens supporting member 61 is an extremely small member, and the errors of the internal and external diameter dimensions thereof affects the optical performance (that is, the quality of a captured image) of the endoscope 100. By constituting the lens supporting member 61 of, for example, a nickel electroformed tube, the endoscope 100 capable of securing high dimensional accuracy and capturing a high-quality image irrespective of small diameter is obtained.

The lens supporting member 61 may be a sheet material or the like in addition to the metal, and the lens supporting member 61 may be positioned as long as the optical axes of the respective lenses 35 of the lens unit 53 are aligned with each other. If the lens unit 53 is covered with the resin, mutual relative positions of the respective lenses 35 are fixed. For this reason, the lens supporting member 61 can be made of a material having a low strength, a small thickness, and a light weight compared with a lens barrel used in order to support the plurality of lenses 35 in the related art. Accordingly, it is possible to contribute to a reduction in diameter of the tip portion 27 in the endoscope 100. In addition, the lens supporting member 61 does not exclude using the same metallic lens barrel as the related art.

The image sensor 29 is constituted of, for example, an imaging device of a small-sized charge coupled device (CCD) or a complementary metal-oxide semiconductor (CMOS) having a square shape as seen from the forward-rearward direction. In the image sensor 29, the light incident from the outside is focused on the imaging surface by the lenses 35 accommodated in the lens supporting member 61. Additionally, in the image sensor 29, the imaging surface is covered with the element cover glass 63. The image sensor 29 is formed in an angular shape (for example, a quadrangular shape). Additionally, the image sensor 29 may not be limited to being formed in the quadrangular shape and may be formed, for example, in a hexagonal shape or in an octagonal shape.

The lens unit 53 and the element cover glass 63 are fixed by a bonding resin. The bonding resin is constituted of, for example, a UV thermosetting resin. The bonding resin has translucency. In a case where the UV thermosetting resin is used as the bonding resin, an outer surface portion can be cured by ultraviolet radiation, and the inside of a filling adhesive that cannot be irradiated with ultraviolet rays can be cured by heat treatment. The bonding resin fixes the lens unit 53, in which the optical axes are made to coincide with the center of the imaging surface, to the element cover glass 63. Accordingly, the lens unit 53 and the image sensor 29 are directly bonded and fixed with the bonding resin, that is, the lens unit 53 and the image sensor 29 are directly attached to each other via the bonding resin. Although the bonding resin requires, for example, the heat treatment in order to obtain final hardness, the bonding resin is an adhesive of a type in which curing proceeds to a certain degree of hardness also by ultraviolet radiation.

In addition, in an endoscope 100, in a case where a light emission surface of each lens 35 that faces the element cover glass 63 is a concave surface, an edge portion that is an annular end surface around the lens 35 is bonded the element cover glass 63. In this case, an outer periphery of the lens 35 and an outer periphery of the lens supporting member 61 may also be simultaneously fixed with the bonding resin. An air space is provided between the lens 35 and the image sensor 29 as the edge portion of the lens 35 is bonded to the element cover glass 63. As the air space is provided between the lens 35 and the image sensor 29, the optical performance of the lens 35 can be enhanced. For example, the refractive index difference of the light emitted from the lens 35 to the air space can be increased, and power for refracting the light is obtained. Accordingly, optical design, such as enhancing resolution and increasing the angle of view, is facilitated. As a result, the quality of an image captured by the endoscope 100 is improved.

A plurality of conductor connecting portions are provided at a rear portion on a back side of the image sensor 29. The conductor connecting portions can be formed of, for example, a land grid array (LGA). The conductor connecting portions include an electrical power connecting portion and a signal connecting portion. The conductor connecting portions are electrically connected to a plurality of electric wires of the transmission cable 25. The plurality of electric wires include, for example, an insulated signal line 65, an insulated power source line 67, and an insulated GND line 69 (refer to FIG. 6). An insulated earth line 71 is provided along the transmission cable 25. In addition, the insulated earth line 71 may be included in the transmission cable 25.

The endoscope 100 includes a linear conductor 73 at the tip portion 27. A tip of the linear conductor 73 extends toward the lens unit side with respect to the image sensor 29, and a proximal end thereof passes through the insertion portion 15. In the linear conductor 73, the conductor may be either a single line or a stranded line. The materials of the conductor include, for example, an aluminum alloy, a copper alloy, and the like. In the linear conductor 73, the conductor may be insulatively covered with vinyl chloride, polyethylene, or the like. A proximal end of the linear conductor 73 passes through the inside of the sheath 43 in the insertion portion 15. The linear conductor 73 may be connected to the plug 17 as it is, may be connected to the insulated earth line 71 in the flexible portion 23, or may be connected to the plug 17 via the insulated earth line 71. In any case, the linear conductor 73 is connected to an insulated earth portion of a circuit 75 to be insulated (refer to FIG. 6) via the plug 17.

A tip of the linear conductor 73 and the tip flange portion 33 are separated from each other. Specifically, the tip of the linear conductor 73 is disposed so as to be separated from, for example, the angular tube portion 55 of the tip flange portion 33. A gap G is secured between a rear end surface of the angular tube portion 55 and the tip of the linear conductor 73. The tip of the linear conductor 73 is coated with, for example, a mold resin 49 having a thickness substantially equivalent to the gap G on the rear end surface of the angular tube portion 55, is inserted into the mold resin 49, and is then fixed to the mold resin 49 with an adhesive 77.

Therefore, in the endoscope 100, the linear conductor 73 is fixed with the adhesive 77 in a state where the tip of the linear conductor 73 and the tip flange portion 33 are separated from each other.

In the endoscope 100, as illustrated in FIG. 3, an outer periphery of the lens unit 53 is molded by the mold portion 45. In the endoscope 100 of Embodiment 1, the linear conductor 73 and the adhesive 77 are simultaneously covered with the mold portion 45.

FIG. 5 is a view as seen from arrow A-A of FIG. 4.

Here, the tip of the linear conductor 73 is disposed between the outer periphery of the circular lens unit 53 surrounded by an angular outline (for example, a quadrangular outline) of the image sensor 29, and corner portions of the image sensor 29. That is, internal corner portions between corners of the angular tube portion 55 and the internal diameter hole 59 are coated with the mold resin 49, and the tip of the linear conductor 73 is fixed to the mold resin 49 with the adhesive 77. In addition, four corner of the angular tube portion 55 and four corners of the image sensor 29 are disposed in the same phases.

Figure 6:
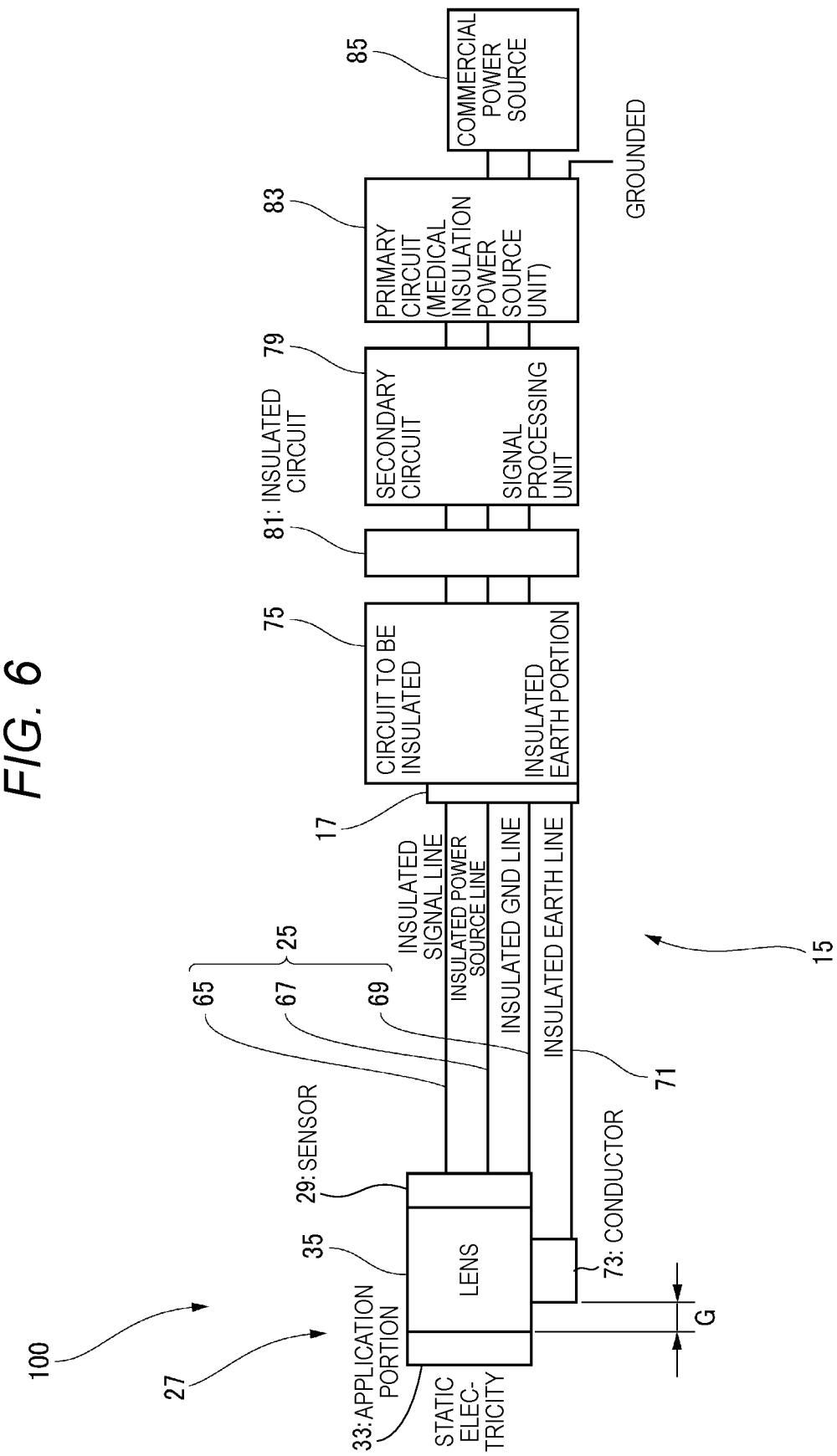
FIG. 6 is a block diagram schematically illustrating the configuration of the endoscopic system in a case where the endoscope of Embodiment 1 is used for medical applications.

FIG. 6 is a block diagram schematically illustrating the configuration of the endoscopic system 11 in a case where the endoscope 100 of Embodiment 1 is used for medical applications.

In the endoscope 100, a front surface of the tip portion 27 serves as a static electricity application portion (static electricity application portion). That is, the tip flange portion 33 serves as the application portion. In other words, when the endoscope 100 is inserted into the examination target during use of (for example, during examination or during surgery), static electricity flows into the tip flange portion 33. The static electricity that has flowed into the tip flange portion 33 flows into the linear conductor 73 via the gap G by discharge, and is allowed to escape from the linear conductor 73 serving as the insulated earth line 71 to the insulated earth portion of the circuit 75 to be insulated via the plug 17. Accordingly, the application of the static electricity to the image sensor (that is, the image sensor 29) is suppressed.

The insulated earth portion is provided at the circuit 75 to be insulated. The circuit 75 to be insulated can also be referred to as a protected circuit for preventing an electric shock to a patient. Additionally, by providing an insulated circuit 81 between the circuit 75 to be insulated, and a secondary circuit 79 having a signal processing unit (driven with DC 10 to 12 V) provided within the video processor 13, a state where the circuit 75 to be insulated and the secondary circuit 79 are electrically insulated is secured. The secondary circuit 79 is connected to a primary circuit 83 to be grounded.

Normally, a power supply device (medical insulation power source unit) having reinforced insulation for medical applications, is used for the primary circuit 83 used for medical apparatuses, and the primary circuit 83 is connected to a commercial power source 85 (for example, AC 100 V).

In a case where the endoscope 100 is used as a medical endoscope, it is necessary to consider preventing inflow of a leakage current to a patient. For that reason, the linear conductor 73 that guides the static electricity, and a patient contacting portion (for example, the tip flange portion 33) are insulated from each other by providing the gap G. The linear conductor 73 that guides the static electricity is connected to the insulated earth portion that sufficiently reduces the leakage current via the electrically insulated circuit 81. In this way, the endoscope 100 protects the image sensor 29 by installing the linear conductor 73 for guiding the static electricity to allow the static electricity to escape from the image sensor 29, between the static electricity application portion and the image sensor 29 to allow the static electricity to escape to the insulated earth portion.

Next, the operation of the above-described configuration will be described.

In the endoscope 100 of Embodiment 1, the tip of the linear conductor 73 extends toward the lens unit 53 side with respect to the image sensor 29. For that reason, the dielectric breakdown strength from a side surface of the lens unit 53 to the tip of the linear conductor 73 can be made smaller that the dielectric breakdown strength from the lens unit 53 to the image sensor 29. The static electricity applied to the tip portion 27 due to the difference in dielectric breakdown strength is discharged to the tip of the linear conductor 73 while flowing into the image sensor 29 is suppressed. That is, by installing the linear conductor 73 that guides the static electricity between the static electricity application portion and the image sensor 29, it is possible to reliably allow the static electricity to escape to the insulated earth portion within the circuit 75 to be insulated via the linear conductor 73 serving as the insulated earth line, or the plug 17, and the image sensor 29 can be exactly protected. In the endoscope 100, since the linear conductor 73 may be disposed to extend toward the lens unit side with respect to the image sensor 29, the structure becomes extremely simple. As a result, the manufacture is facilitated, and particularly, a reduction in size and a reduction in diameter is facilitated compared to a structure in which a related-art projection portion or metallic pipe is provided as in the above-described WO2013/031276.

Additionally, in the endoscope 100, it is possible to guide the application of the static electricity to the tip flange portion 33 by providing the tip flange portion 33 having conductivity on the front surface of the tip portion 27. For this reason, it is possible to more reliably allow the static electricity to escape to the insulated earth portion by carrying disposing the tip of the linear conductor 73 in proximity to the tip flange portion 33.

Additionally, in the endoscope 100, the linear conductor 73 that guides the static electricity, and the patient contacting portion (particularly, the tip flange portion 33) are insulated from each other by this separation. The linear conductor 73 that guides the static electricity is connected to the earth portion that sufficiently reduces the leakage current via the electrically insulated circuit 81. Therefore, the endoscope 100 can sufficiently reduce the leakage current to a patient in medical applications.

Additionally, in the endoscope 100, since the linear conductor 73 is fixed to the tip flange portion 33 by the mold resin 49 and the adhesive 77, a separation distance can be set with high accuracy in a case where the tip of the linear conductor 73 is separated from the tip flange portion 33. Additionally, in a case where the linear conductor 73 is covered with the mold portion 45, the linear conductor 73 can be fixed to a desired position in advance. Thus, the positional deviation of the linear conductor 73 during pouring of the mold resin can be suppressed to facilitate a molding step.

Additionally, in the endoscope 100, particularly, in a case where the optical fibers 39 for guiding light are disposed between a side portion of the image sensor 29 and the outer periphery of the mold portion 45, any interference between the linear conductor 73 and the optical fibers 39 can be avoided. The linear conductor 73 can be easily disposed or fixed while avoiding any interference with the optical fibers 39.

Moreover, in the endoscope 100, the linear conductor 73 can be reliably fixed to the tip portion 27 by embedding the linear conductor 73 in the mold portion 45. For this reason, the endoscope 100 can enhance the fixed strength of the linear conductor 73 against the tension generated in the linear conductor 73 as the insertion portion 15 is bent during operation.

Embodiment 2

Next, an endoscope 200 of Embodiment 2 will be described.

Figure 7:
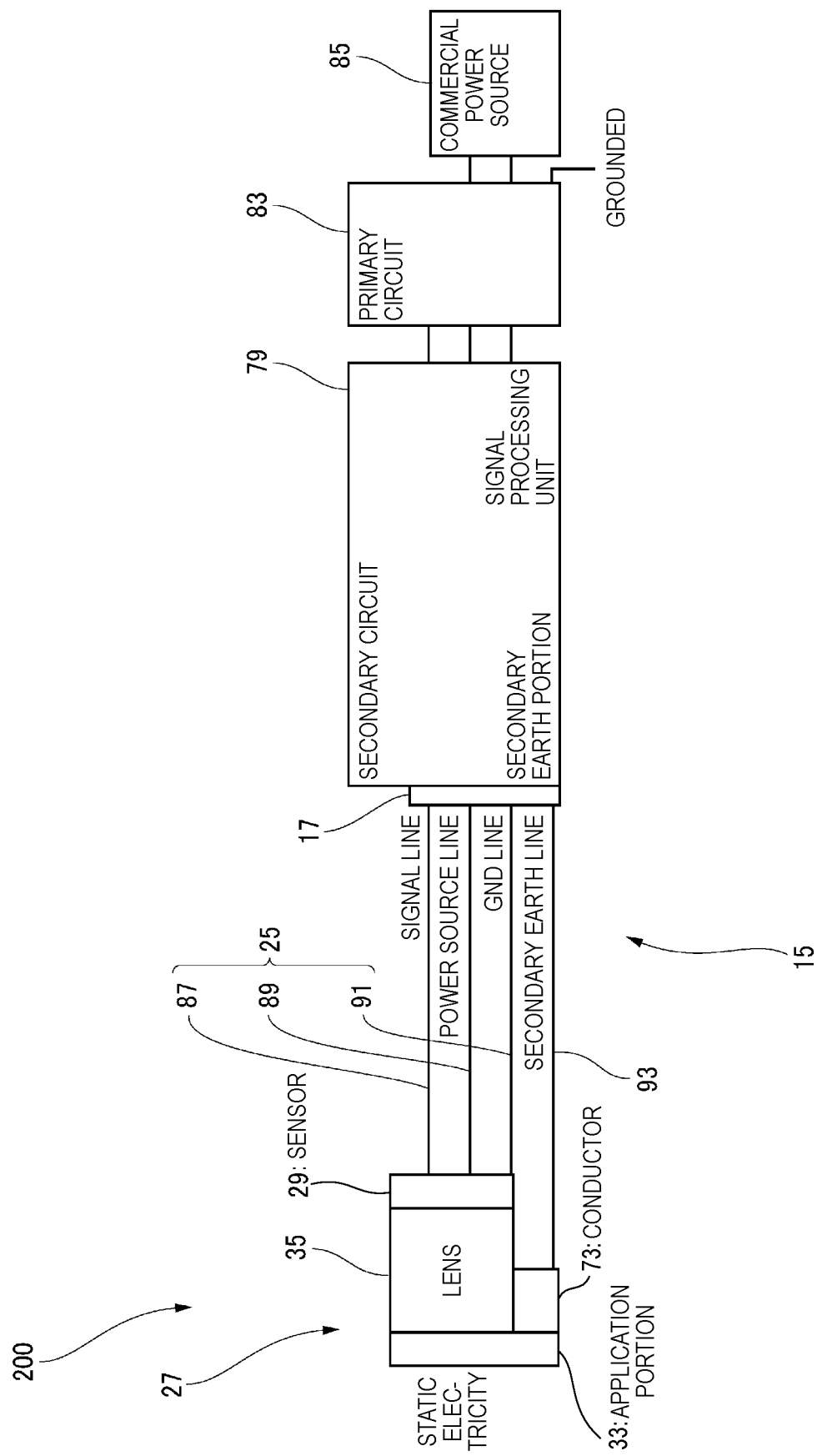
FIG. 7 is a block diagram schematically illustrating the configuration of the endoscopic system in a case where the endoscope of Embodiment 1 is used for industrial applications.

FIG. 7 is a block diagram schematically illustrating the configuration of the endoscopic system 11 in a case where the endoscope 200 of Embodiment 2 is used for industrial applications. In addition, in Embodiment 2, the same members as the members illustrated in FIGS. 1 to 6 will be designated by the same reference signs, and duplicate description will be omitted.

In the endoscope 200 of Embodiment 2, the tip of the linear conductor 73 and the tip flange portion 33 are electrically connected to each other. The linear conductor 73 is conductively connected to the angular tube portion 55 with, for example, solder. Additionally, the conductive connection between the linear conductor 73 and the angular tube portion 55 may be further firmly fixed not only with solder but with the adhesive 77. The transmission cable 25 includes a signal line 87, a power source line 89, and a GND line 91. The linear conductor 73 serving as a secondary earth line 93 is provided in the transmission cable 25. In addition, the secondary earth line 93 may be included in the transmission cable 25. The transmission cable 25 and the secondary earth line 93 are connected to the secondary circuit 79 having a secondary earth portion and the signal processing unit via the plug 17. The secondary circuit 79 is connected to the primary circuit 83 to be grounded. The primary circuit 83 is connected to the commercial power source 85. The other configuration is the same as the schematic block diagram (refer to FIG. 6) of the endoscopic system 11 including the endoscope 100 of Embodiment 1.

According to the endoscope 200 of Embodiment 2, in the industrial applications that can allow a certain leakage current, the static electricity can be reliably guided by conducting the tip of the linear conductor 73 to the static electricity application portion (tip flange portion 33). The linear conductor 73 that guides the static electricity can be connected to an earth portion having low impedance. The industrial endoscope 200 can have a simpler configuration compared to the medical endoscope 100, and can also be easily manufactured.

Embodiment 3

Next, endoscopes 300 and 300A of Embodiment 3 will be described.

Figure 8:
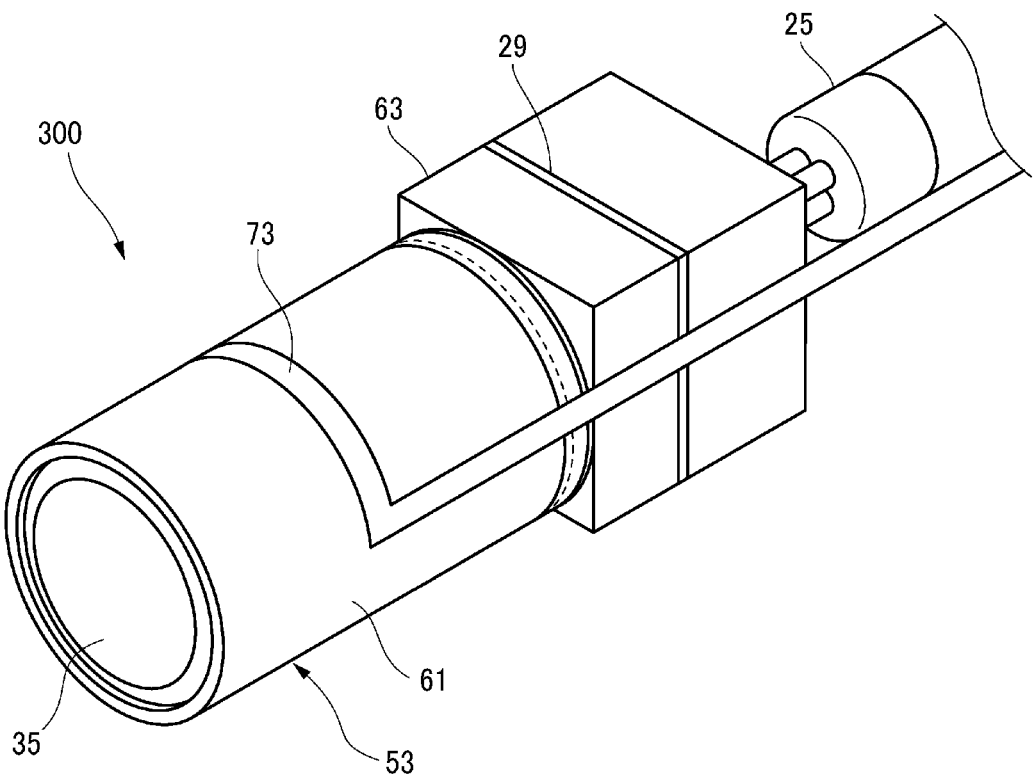
FIG. 8 is a perspective view of main portions of a configuration example in which a tip of a linear conductor in an endoscope of Embodiment 3 is disposed in a circumferential direction.

FIG. 8 is a perspective view of main portions of a configuration example in which the tip of the linear conductor 73 in the endoscope 300 of Embodiment 3 is disposed in the circumferential direction. In addition, in Embodiment 3, the same members as the members illustrated in FIGS. 1 to 6 will be designated by the same reference signs, and duplicate description will be omitted.

In the endoscope 300 of Embodiment 3, the tip of the linear conductor 73 is formed along a portion of the lens unit 53 in the circumferential direction. The other configuration is the same as the endoscope 100 of Embodiment 1.

According to the endoscope 300 of Embodiment 3, since the tip of the linear conductor 73 extends also in the circumferential direction, the static electricity can be easily guided to the linear conductor 73.

Figure 9:
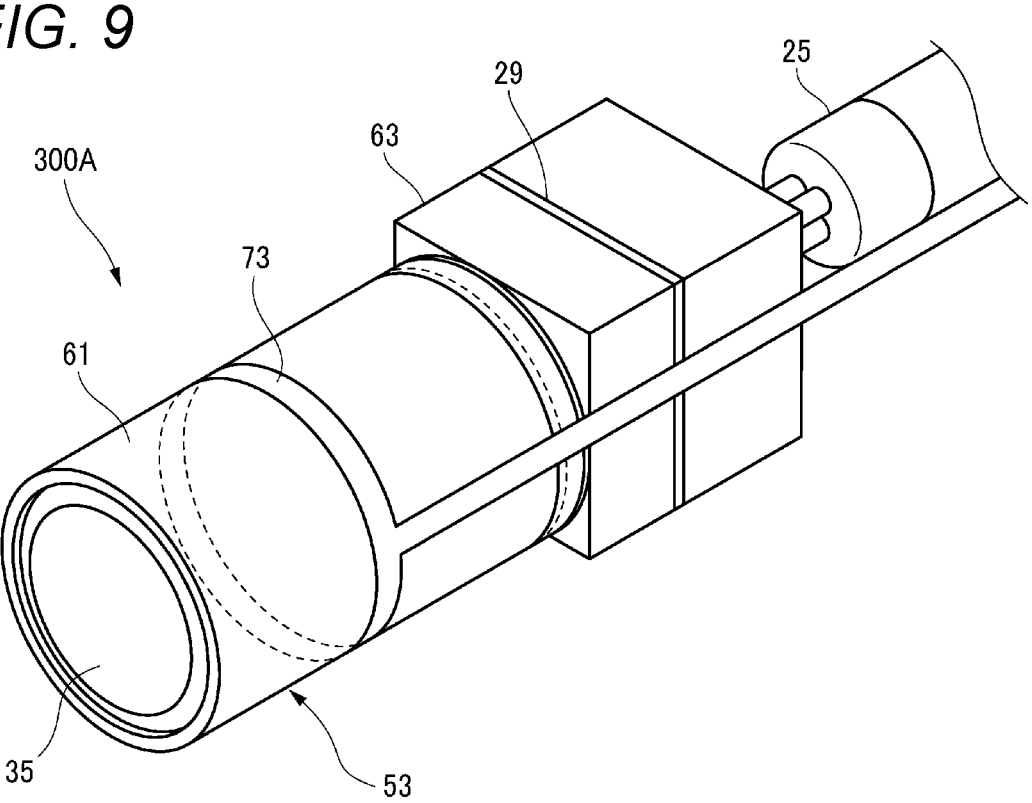
FIG. 9 is a perspective view of main portions of a configuration example in which the tip of the linear conductor in the endoscope of Embodiment 3 is disposed at the entire circumference in the circumferential direction.

FIG. 9 is a perspective view of main portions of a configuration example in which the tip of the linear conductor 73 in the endoscope 300A of Embodiment 3 is disposed at the entire circumference in the circumferential direction.

Additionally, in the endoscope 300A of Embodiment 3, the tip of the linear conductor 73 is formed along the entire circumference of the lens unit 53 in the circumferential direction. The other configuration is the same as the endoscope 100 of Embodiment 1.

According to the endoscope 300A of Embodiment 3, since the tip of the linear conductor 73 extends over the entire circumference of the lens unit 53, the static electricity can be easily guided to the linear conductor 73.

Embodiment 4

Next, an endoscope 400 of Embodiment 4 will be described.

Figure 10:
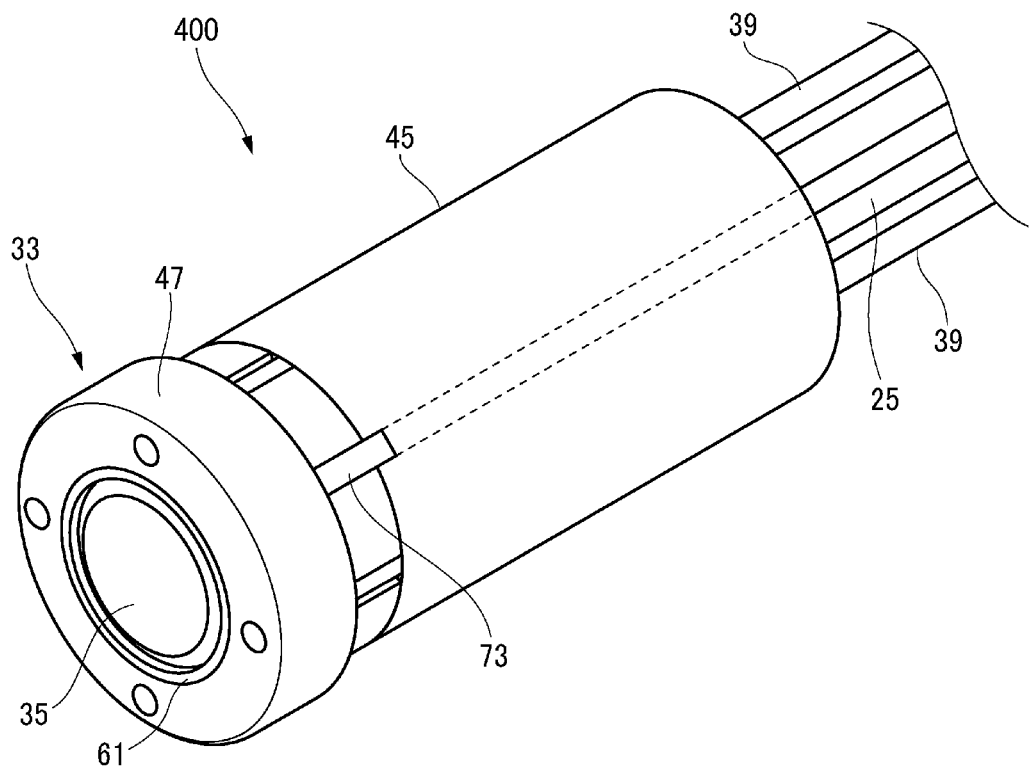
FIG. 10 is a perspective view of main portions of a configuration example in which a linear tip of a linear conductor in an endoscope of Embodiment 4 is disposed outside a mold portion.

FIG. 10 is a perspective view of main portions of a configuration example in which a linear tip of the linear conductor 73 in the endoscope 400 of Embodiment 4 is disposed outside the mold portion 45.

Figure 11:
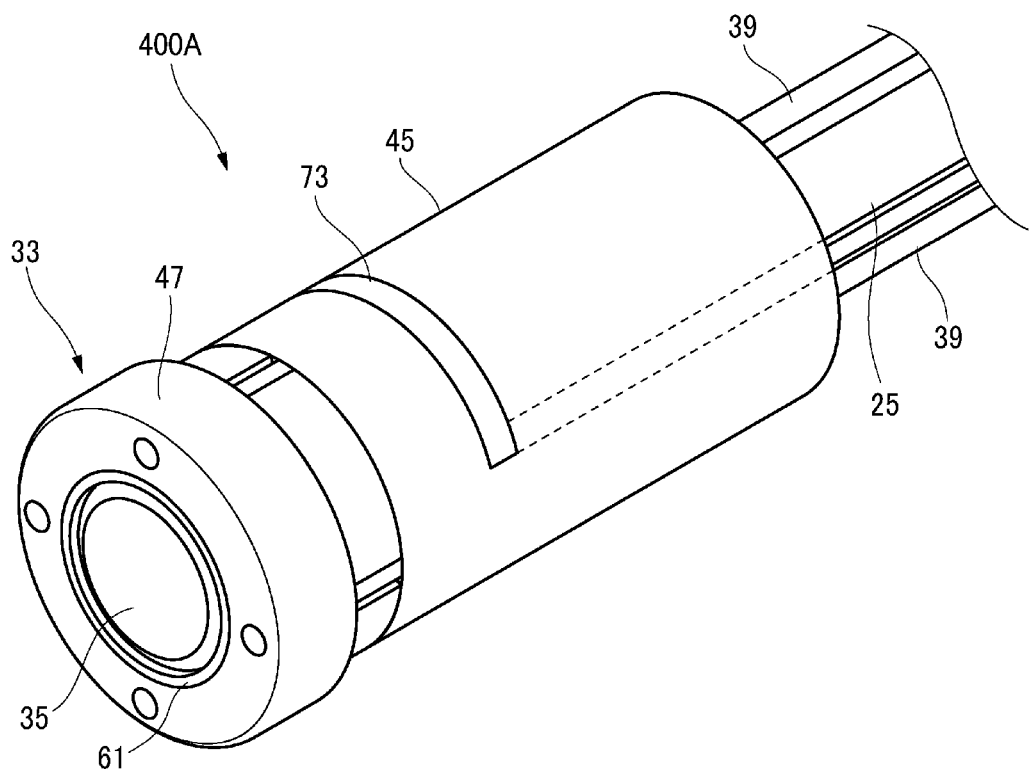
FIG. 11 is a perspective view of main portions of a configuration example in which a circumferential tip of the linear conductor in an endoscope of Embodiment 4 is disposed outside the mold portion.

FIG. 11 is a perspective view of main portions of a configuration example in which a circumferential tip of the linear conductor 73 in an endoscope 400A of Embodiment 4 is disposed outside the mold portion 45. In addition, in Embodiment 4, the same members as the members illustrated in FIGS. 1 to 6 will be designated by the same reference signs, and duplicate description will be omitted.

In the endoscope 400 of Embodiment 4, an outer periphery of the lens unit 53 is molded by the mold portion 45, and the tip of the linear conductor 73 is disposed outside the mold portion 45. The tip of the linear conductor 73 disposed outside the mold portion 45 may be exposed in a straight line as in the endoscope 400 illustrated in FIG. 10, and may be exposed along the circumference of the lens unit 53 as in the endoscope 400A illustrated in FIG. 11. The other configuration is the same as the endoscope 100 of Embodiment 1.

According to the endoscopes 400 and 400A of this embodiment, the portions of the linear conductor 73 other than the tip is fixed by the mold portion 45, and the tip of the linear conductor 73 is disposed outside the mold portion 45.

Thus, the guidance effect of the static electricity can also be enhanced while the fixation thereof is reliably performed.

Therefore, according to the endoscope 100, the endoscope 200, the endoscope 300, the endoscope 300A, the endoscope 400, and the endoscope 400A of the embodiments, a reduction in diameter can be easily achieved with a simple structure while the image sensor 29 is protected by releasing static electricity.

Embodiment 5

Next, an endoscope 500 of Embodiment 5 will be described.

Figure 12:
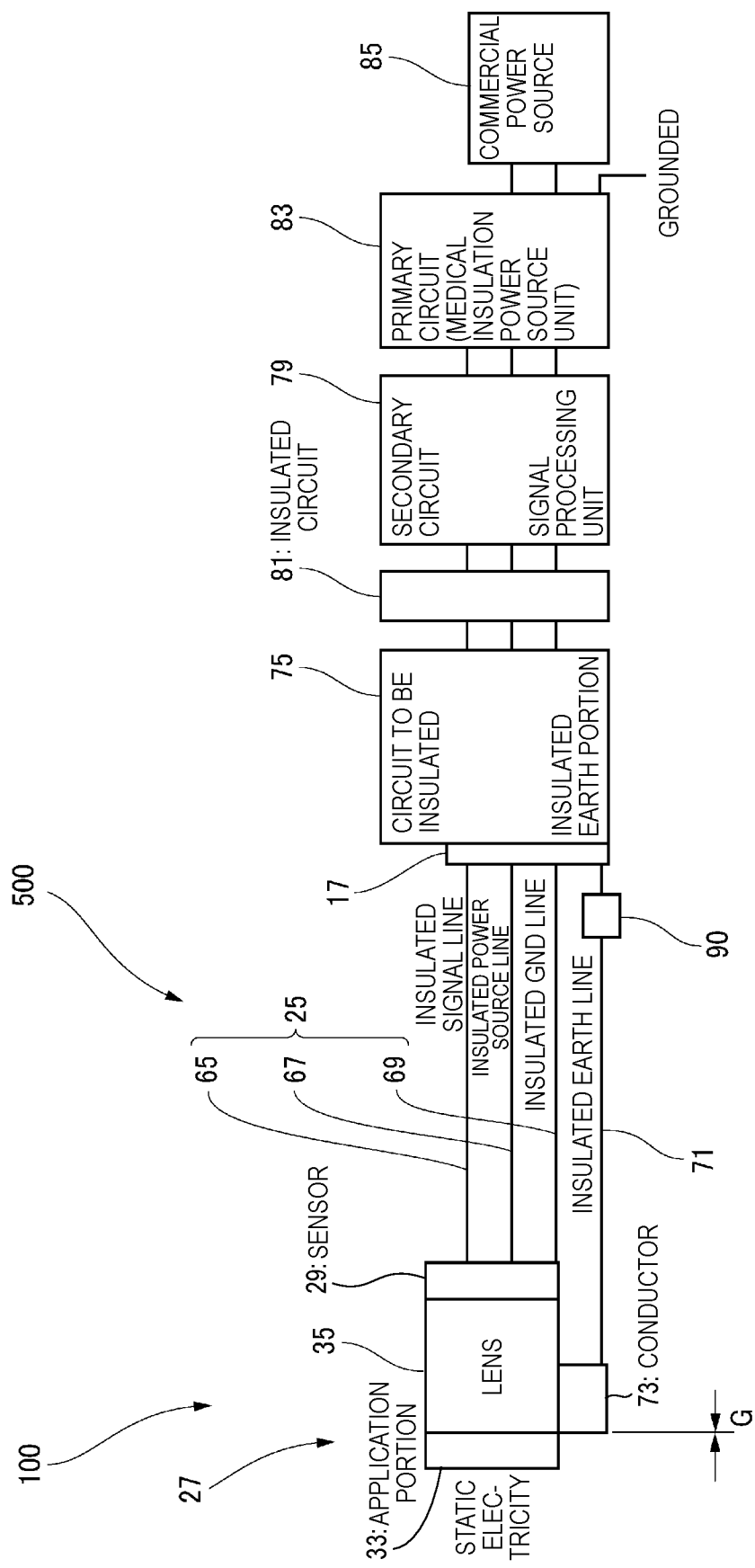
FIG. 12 is a block diagram schematically illustrating the configuration of an endoscopic system in a case where an endoscope of Embodiment 5 is used for medical applications.

FIG. 12 is a block diagram schematically illustrating the configuration of the endoscopic system in a case where the endoscope 500 of Embodiment 5 is used for medical applications. In addition, in Embodiment 5, the same members as the members illustrated in FIGS. 1 to 6 will be designated by the same reference signs, and duplicate description will be omitted.

In the endoscope 500 of Embodiment 5, a sufficient gap G (for example, refer to the gap G illustrated in FIG. 4) is not provided between the rear end surface of the angular tube portion 55 and the tip of the linear conductor 73. Additionally, an electro static discharge (ESD) suppressor 90 (an example of a surge absorber) is inserted between the linear conductor 73 and the insulated earth line 71, and the insulated earth portion.

The ESD suppressor 90 is an example of a surge absorber that is a protective element four countermeasures against a high voltage, and protects an electronic apparatus (that is, a circuit to be protected) from static electricity by utilizing the characteristic that the resistance value decreases abruptly if a high voltage, such as the static electricity, is applied. Additionally, the ESD suppressor 90 reduces the amount of a leakage current from the apparatus of the endoscope 500 by utilizing the characteristic having a large resistance value if a voltage lower than the static electricity is applied.

Figure 13A:
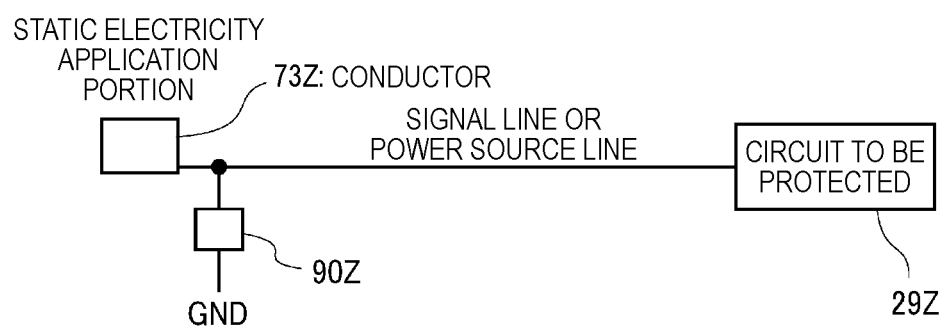
FIG. 13A is a block diagram schematically illustrating a first usage example of an ESD suppressor related to a comparative example.
Figure 13B:
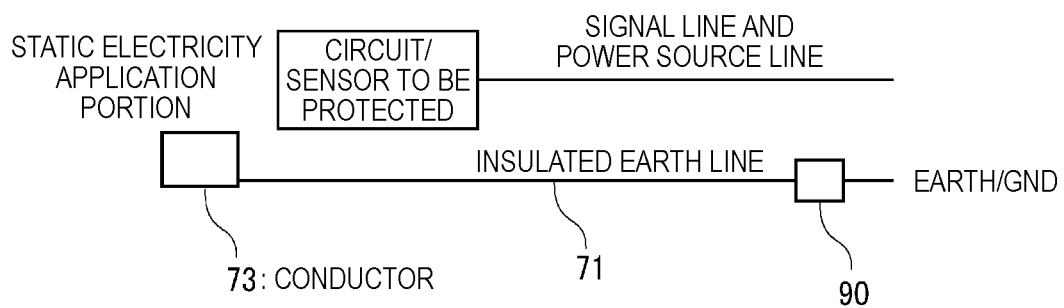
FIG. 13B is a block diagram schematically illustrating a second usage example of an ESD suppressor related to Embodiment 5.
Figure 14:
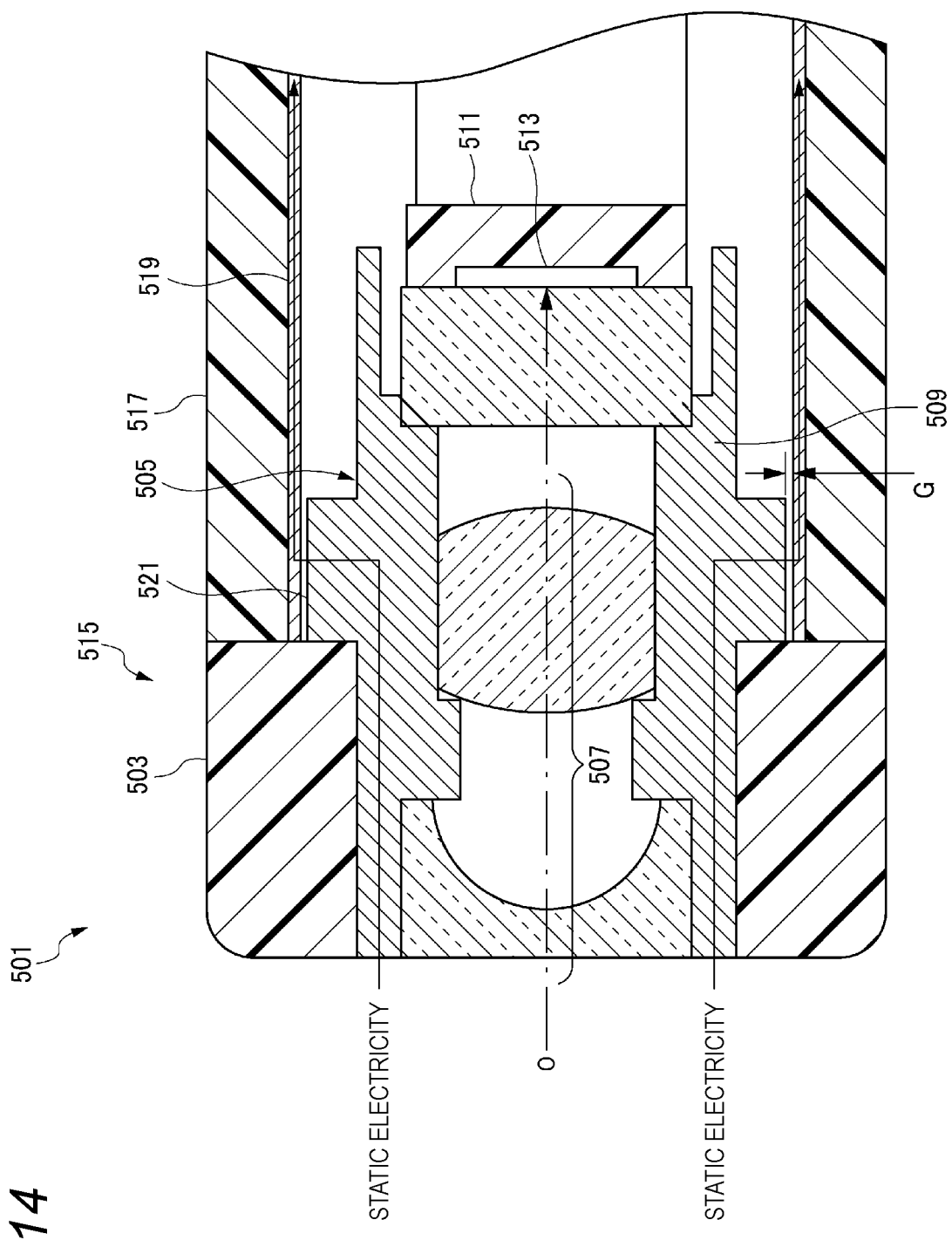
FIG. 14 is a sectional view illustrating the configuration of a tip portion of a related-art endoscope.

FIG. 13A is a block diagram schematically illustrating a first usage example of an ESD suppressor related to a comparative example. FIG. 13B is a block diagram schematically illustrating a second usage example of the ESD suppressor related to Embodiment 5.

As illustrated in FIG. 13A, an ESD suppressor 90z is disposed so as to be inserted into the ground (GND) from a location as close to the static electricity application portion as possible in a signal line or a power source line to which the static electricity is applied, as a general usage. Accordingly, in a case where a low voltage is applied, the ESD suppressor 90z functions as a resistor having a large resistance value, and causes a voltage or electric current from a conductor 73z to be supplied to a circuit 29z to be protected via the signal line or the power source line. On the other hand, in a case where a high voltage, such as the static electricity, is applied, the ESD suppressor 90z can allow the static electricity to escape to the ground (GND), and can prevent the static electricity from being applied to the circuit 29z so as to protect the circuit 29z.

Meanwhile, as illustrated in FIG. 13B, in Embodiment 5, the ESD suppressor 90 is inserted between the linear conductor 73 and the insulated earth line 71, and the insulated earth portion of the circuit 75 to be insulated. Accordingly, in a case where a low voltage is applied, the ESD suppressor 90 functions as resistor having a large resistance value, and can cut off the leakage current from the apparatus of the endoscope 500 to reduce leakage of the leakage current to the tip flange portion 33 serving as the patient contacting portion. Additionally, when a high voltage, such as the static electricity, is applied, the ESD suppressor 90 operates to allow the static electricity to escape from the linear conductor 73 and the insulated earth line 71 to the insulated earth portion of the circuit 75 to be insulated by utilizing the characteristic that the resistance value is abruptly lowered. Therefore, even in a case where a sufficient gap G (for example, refer to the gap G illustrated in FIG. 4) is not provided between the rear end surface of the angular tube portion 55 and the tip of the linear conductor 73, the ESD suppressor 90 can suppress that the static electricity is applied to a circuit (for example, the image sensor 29) to be protected, such as a sensor. That is, according to the endoscope 500 of Embodiment 5, by virtue of the insertion of the ESD suppressor 90, a path along which the static electricity is allowed to escape can be secured and insulation can be guaranteed to reduce the leakage current.

In the endoscope 500) of Embodiment 5, the ESD suppressor 90 serving as the protective element that cuts off the leakage current to the tip portion 27 is disposed between the linear conductor 73 and the circuit 75 to be insulated electrically insulated from the tip portion 27. Accordingly, even if a sufficient gap G is not provided at the tip (specifically, the rear end surface of the angular tube portion 55 and the tip of the linear conductor 73) of the endoscope 500, the ESD suppressor 90 is inserted before the ground connection of the linear conductor 73. Accordingly, insulation can be guaranteed to reduce the leakage current while securing the path along which the static electricity is allowed to escape.

Although the various embodiments have been described above referring to the drawings, it is needless to say that the invention is not limited to the embodiments related to the present disclosure. Those skilled in the art will appreciate that various modifications or alterations can be conceived within the scope set forth in the claims and these also naturally fall within the technical scope of the present disclosure. Additionally, configurations in which respective constituent elements in the above-described embodiments are arbitrarily combined may be adopted without departing from the spirit of the invention.

The present disclosure is useful as endoscopes in which a reduction in diameter of the insertion tip portion is facilitated with a simple structure while the image sensor is protected by releasing the static electricity.

The present invention is based upon Japanese Patent Application (Patent Application No. 2017-150016) filed on Aug. 2, 2017, the contents of which are incorporated herein by reference.

What is claimed is:

1. An endoscope comprising:
    an insertion portion that has a tip portion to be inserted into an examination target from a tip side of the tip portion;
    a lens that is disposed at the tip portion;
    a tip flange portion that is disposed on a front outermost surface of the tip portion and has electrical conductivity, wherein an internal diameter hole of the tip flange portion supports a part of the lens at the tip side;
    an image sensor that is disposed on an opposite side to the tip side of the tip portion with respect to the lens;
    an electrically-insulative circuit; and
    a linear conductor electrically connected to the electrically-insulative circuit via an insulated earth line, and that has a tip disposed at the tip side with respect to the image sensor and has a proximal end which is extended from the tip through inside the insertion portion,
    wherein the tip of the linear conductor and the tip flange portion are electrically connected to each other.
2. The endoscope according to claim 1,
    wherein the tip of the linear conductor and the tip flange portion are disposed so as to be separated from each other.
3. The endoscope according to claim 2,
    wherein the tip of the linear conductor and the tip flange portion are fixed to each other with an adhesive.
4. The endoscope according to claim 2,
    wherein the tip of the linear conductor extends along a part of circumferential surface of the lens in a circumferential direction.
5. The endoscope according to claim 2,
    wherein the tip of the linear conductor extends along an entire circumference of the lens in a circumferential direction.
6. The endoscope according to claim 2,
    wherein the tip of the linear conductor and the tip flange portion are disposed so as to be separated from each other by a resin.
7. The endoscope according to claim 1,
    wherein the tip of the linear conductor is disposed between an outer periphery of a circular lens and a corner portion of the image sensor, and
    wherein the circular lens is surrounded by an angular outline of the image sensor.
8. The endoscope according to claim 1,
    wherein an outer periphery of the lens is molded by a mold portion, and
    wherein at least a portion of the tip of the linear conductor is covered with the mold portion.
9. The endoscope according to claim 1,
    wherein an outer periphery of the lens is molded by a mold portion, and
    wherein the tip of the linear conductor is disposed outside the mold portion.
10. The endoscope according to claim 1, further comprising:
    a protective element that is disposed between the linear conductor, wherein the electrically-insulative circuit is electrically insulated from the tip portion.
11. The endoscope according to claim 10, wherein the protective element cuts off a leakage current leaking in the tip portion.
12. The endoscope according to claim 1, wherein the electrically-insulative circuit is a protected circuit that prevents an electric shock to a patient.
13. The endoscope according to claim 1, wherein the electrically-insulative circuit suppresses static electricity from the tip portion.

* * * * *